(12) United States Patent
Zuhars

(10) Patent No.: US 8,652,148 B2
(45) Date of Patent: Feb. 18, 2014

(54) TRACKED CARTILAGE REPAIR SYSTEM

(75) Inventor: Joel Zuhars, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 212 days.

(21) Appl. No.: 13/031,457

(22) Filed: Feb. 21, 2011

(65) Prior Publication Data

US 2011/0208256 A1    Aug. 25, 2011

Related U.S. Application Data

(60) Provisional application No. 61/308,176, filed on Feb. 25, 2010.

(51) Int. Cl.
*A61B 19/00* (2006.01)

(52) U.S. Cl.
USPC .......................... 606/130; 606/86 R; 600/426

(58) Field of Classification Search
USPC .......... 606/86 R, 87–89, 96–97, 99; 600/424; 700/97–98, 118, 159, 161
See application file for complete search history.

(56) References Cited

U.S. PATENT DOCUMENTS

| | | | |
|---|---|---|---|
| 5,432,703 A | | 7/1995 | Clynch et al. |
| 5,552,992 A | * | 9/1996 | Hunter .......................... 700/118 |
| 5,560,096 A | * | 10/1996 | Stephens .......................... 29/558 |
| 5,769,078 A | | 6/1998 | Kliegis |
| 5,781,652 A | * | 7/1998 | Pratt .............................. 382/128 |
| 5,824,085 A | * | 10/1998 | Sahay et al. .................. 128/898 |
| 6,402,782 B1 | | 6/2002 | Sibbald et al. |
| 6,591,581 B2 | | 7/2003 | Schmieding |
| 6,610,067 B2 | | 8/2003 | Tallarida et al. |
| 6,757,582 B2 | | 6/2004 | Brisson et al. |
| 6,865,442 B1 | * | 3/2005 | Jared .............................. 700/191 |
| 6,932,842 B1 | * | 8/2005 | Litschko et al. ........... 623/16.11 |
| 7,029,479 B2 | | 4/2006 | Tallarida et al. |
| 7,314,048 B2 | | 1/2008 | Couture et al. |
| 7,618,451 B2 | * | 11/2009 | Berez et al. ................. 623/14.12 |
| 7,704,254 B2 | | 4/2010 | Walen |
| 7,715,602 B2 | * | 5/2010 | Richard ........................ 382/128 |
| 7,794,462 B2 | | 9/2010 | May et al. |
| 8,234,097 B2 | * | 7/2012 | Steines et al. ..................... 703/1 |

(Continued)

FOREIGN PATENT DOCUMENTS

| | | |
|---|---|---|
| WO | WO2004/016178 A2 | 2/2004 |
| WO | WO2009/061825 A1 | 5/2009 |
| WO | WO2009/094646 A2 | 7/2009 |

*Primary Examiner* — Todd Manahan
*Assistant Examiner* — Jessica Weiss
(74) *Attorney, Agent, or Firm* — Schwegman, Lundberg & Woessner, P.A.

(57) ABSTRACT

A system and method for repairing an area of defective tissue reduces the removal of healthy tissue at the margins of the defect. During excision of diseased or damaged tissue, the system tracks the movement and function of a tissue resection tool within a monitored surgical space. This movement is continuously recorded to create a three-dimensional set of data points representative of the excised volume of tissue. This data set is then communicated to a custom implant forming device which creates a custom implant sized to fit the void created by the excision. The system and method of the present disclosure allows a surgeon to exercise intraoperative control over the specific shape, volume and geometry of the excised area. Moreover, the surgeon may utilize a "freehand" resection method to excise only that tissue deemed to be diseased and/or damaged, because the custom-formed implant will accommodate an irregularly-shaped resection volume.

22 Claims, 6 Drawing Sheets

(56) References Cited

U.S. PATENT DOCUMENTS

| | | |
|---|---|---|
| 2003/0216669 A1 | 11/2003 | Lang et al. |
| 2004/0172044 A1 | 9/2004 | Grimm et al. |
| 2004/0236342 A1 | 11/2004 | Ferree et al. |
| 2004/0243148 A1 | 12/2004 | Wasielewski |
| 2005/0171553 A1 | 8/2005 | Schwarz et al. |
| 2005/0209598 A1 | 9/2005 | Grimm et al. |
| 2006/0036148 A1 | 2/2006 | Grimm |
| 2006/0122618 A1 | 6/2006 | Claypool et al. |
| 2007/0066917 A1 | 3/2007 | Hodorek et al. |
| 2007/0156157 A1 | 7/2007 | Nahum et al. |
| 2007/0213692 A1 | 9/2007 | Neubauer et al. |
| 2007/0239153 A1 | 10/2007 | Hodorek et al. |
| 2007/0255288 A1 | 11/2007 | Mahfouz et al. |
| 2008/0009697 A1 | 1/2008 | Haider et al. |
| 2008/0015677 A1 | 1/2008 | Glossop et al. |
| 2008/0065098 A1 | 3/2008 | Larkin |
| 2008/0119860 A1 | 5/2008 | McCarthy |
| 2008/0140081 A1 | 6/2008 | Heavener et al. |
| 2008/0161824 A1 | 7/2008 | McMillen |
| 2008/0306490 A1* | 12/2008 | Lakin et al. .................. 606/130 |
| 2009/0048597 A1 | 2/2009 | Heavener et al. |
| 2009/0062804 A1 | 3/2009 | Runquist et al. |
| 2009/0112213 A1 | 4/2009 | Heavener et al. |
| 2009/0182226 A1 | 7/2009 | Weitzner et al. |
| 2009/0247863 A1 | 10/2009 | Proulx et al. |
| 2009/0248044 A1 | 10/2009 | Amiot et al. |
| 2009/0258101 A1* | 10/2009 | Linares ........................ 425/142 |
| 2009/0270868 A1* | 10/2009 | Park et al. ...................... 606/87 |
| 2009/0299477 A1 | 12/2009 | Clayton et al. |
| 2010/0049148 A1 | 2/2010 | Siniaguine |
| 2010/0063523 A1 | 3/2010 | Menard et al. |
| 2011/0196377 A1 | 8/2011 | Hodorek |
| 2011/0257653 A1* | 10/2011 | Hughes et al. ................. 606/79 |

* cited by examiner

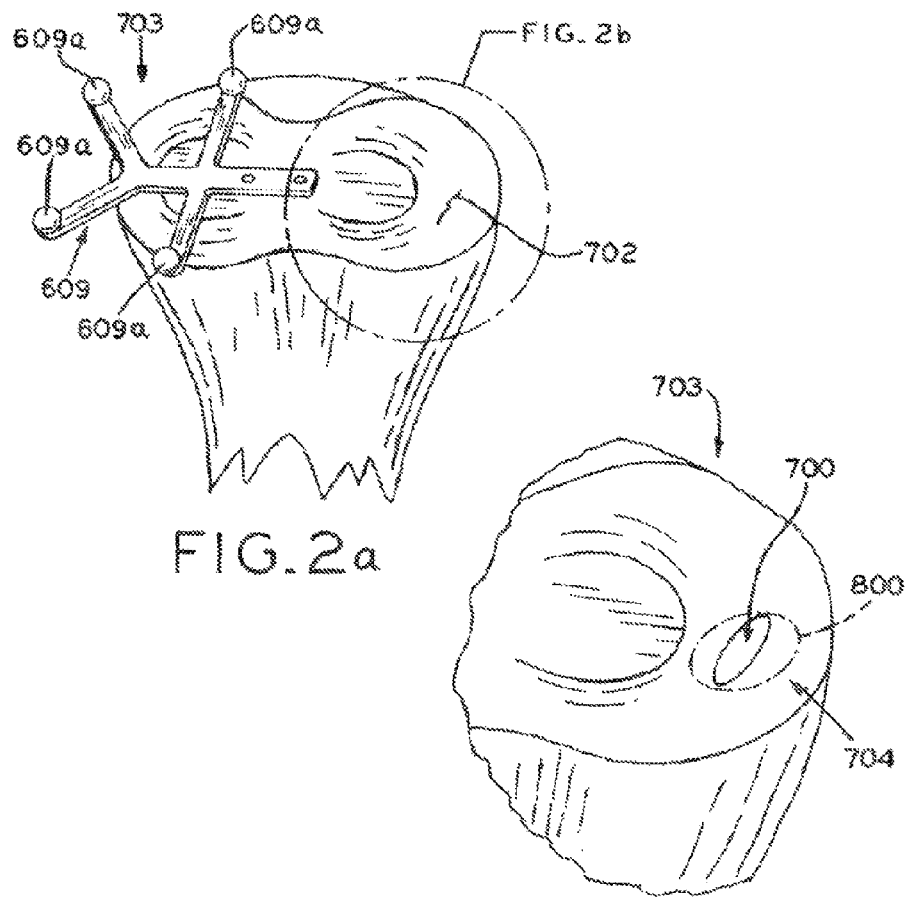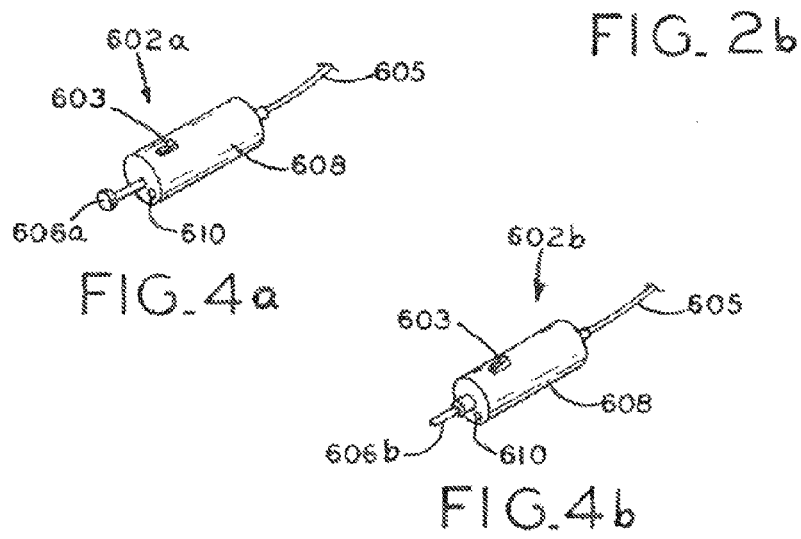

TRACKED CARTILAGE REPAIR SYSTEM

CROSS REFERENCE TO RELATED APPLICATIONS

This application claims the benefit under 35 U.S.C. §119 (e) of U.S. Provisional Patent Application Ser. No. 61/308,176, filed Feb. 25, 2010, the entire disclosure of which is hereby expressly incorporated herein by reference.

BACKGROUND

1. Technical Field

The present disclosure relates to tissue repair and replacement. More particularly, the present disclosure relates to a surgical system for repairing a tissue defect and a method for utilizing the same.

2. Description of the Related Art

Damage to anatomical tissues, i.e. bone and cartilage, may result from trauma, aging or disease, for example. Such damage may result in pain and/or restricted mobility, which in turn may necessitate surgical intervention to repair the damaged tissues. However, some anatomical tissues may require lengthy periods of time to heal or may have limited capability to heal on their own.

Various techniques have been developed to repair tissue damage, such as procedures for joint arthroplasty procedures in which one or more of the articular surfaces of the joint are replaced. In other cases, where only a portion of a particular articular surface needs replacement, a patch or plug of synthetic cartilage and/or bone is implanted in a void created by excision of the damaged tissue. Still other methods, such as mosaicplasty and osteochondral autograft transfer, harvest viable natural cartilage from one area of the body and implant it at the site of the excised damaged tissue.

Where a small area of tissue is removed to repair a defect or injury affecting only a portion of an articular surface, one potential method is to remove a cylinder of tissue large enough to encompass the defect, and then implant a pre-made prosthetic plug sized to fit the cylindrical void created by the resection. However, use of this method for elongate defects, such as hairline fractures or irregularly shaped diseased tissue profiles, may result in the removal of a large proportion of healthy tissue material. In order to reduce the removal of healthy tissue, smaller cylindrical excisions can be serially arranged along the extent of an elongate defect, and smaller cylindrical plugs can then be placed in a line along the resected area.

SUMMARY

The present disclosure provides a system and method for repairing an area of defective tissue which reduces the removal of healthy tissue at the margins of the defect. During excision of diseased or damaged tissue, the system tracks the movement and function of a tissue resection tool within a monitored surgical space. This movement is continuously recorded to create a three-dimensional set of data points representative of the excised volume of tissue. This data set is then communicated to a custom implant forming device which creates a custom implant sized to fit the void created by the excision. The system and method of the present disclosure allows a surgeon to exercise intraoperative control over the specific shape, volume and geometry of the excised area. Moreover, the surgeon may utilize a "freehand" resection method to excise only that tissue deemed to be diseased and/or damaged, because the custom-formed implant will accommodate an irregularly-shaped resection volume.

According to one embodiment thereof, the present disclosure provides a system for repairing a tissue defect, the system comprising: a resection tool having an operative end adapted to resect anatomical tissue; at least one positional marker in a known spatial relationship to the resection tool, the at least one positional marker forming an emanated signal indicative of at least one of a position and an orientation of the operative end of the resection tool, such that movement of the resection tool creates a plurality of data points representative of a volume; a controller communicatively connected to the at least one positional marker and operable to receive the emanated signal, the controller including software adapted to translate the emanated signal into implant forming commands; and an implant forming system which utilizes the implant forming commands to form a custom implant sized to replicate the volume represented by the plurality of data points.

In one aspect thereof, the system provides a detector monitoring a surgical space, the detector operable to detect the emanated signal within the monitored surgical space, wherein the at least one positional marker generates the emanated signal. In another aspect, the system provides a detector monitoring a surgical space, the detector operable to detect the emanated signal within the monitored surgical space; and a signal generator producing an ambient signal within the monitored surgical space, wherein the at least one positional marker reflects at least a portion of the ambient signal to create the emanated signal.

According to another embodiment thereof the present disclosure provides a method of repairing a tissue defect in an anatomical structure, the method comprising the steps of removing a portion of the anatomical structure to create a void having a first shape, the portion including the tissue defect; determining a second shape corresponding to the first shape of the void; and after the step of determining a second shape, manufacturing an implant having the second shape for placement within the void, the second shape generally matching the first shape.

According to yet another embodiment thereof, the present disclosure provides a method system for repairing a tissue defect within a monitored surgical space, the system comprising: means for resecting tissue to create a void having a void size and void shape, the means for resecting comprising: an operative end; and a positional marker in a known spatial relationship to the operative end; means for detecting movement of the positional marker within the monitored surgical space, the means for detecting movement producing a signal; means for converting the signal into implant forming commands; and means for using the implant forming commands to form a custom implant, wherein the custom implant has an implant size corresponding to the void size and an implant shape corresponding to the void shape.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 2a is a perspective view of a proximal portion of a tibia, in which the tibial articular surface has an elongate tissue defect;

FIG. 2b is a partial perspective view of the proximal tibia shown FIG. 2a, illustrating an irregularly-shaped implant filling a correspondingly shaped void after excision of the tissue defect shown in FIG. 2a;

FIG. 4a is a perspective view of a cutting instrument in accordance with the present disclosure;

FIG. 4b is a perspective view of another cutting instrument in accordance with the present disclosure;

Corresponding reference characters indicate corresponding parts throughout the several views. The exemplifications set out herein illustrate exemplary embodiments of the disclosure and such exemplifications are not to be construed as limiting the scope of the disclosure in any manner.

DETAILED DESCRIPTION

Figure 1:
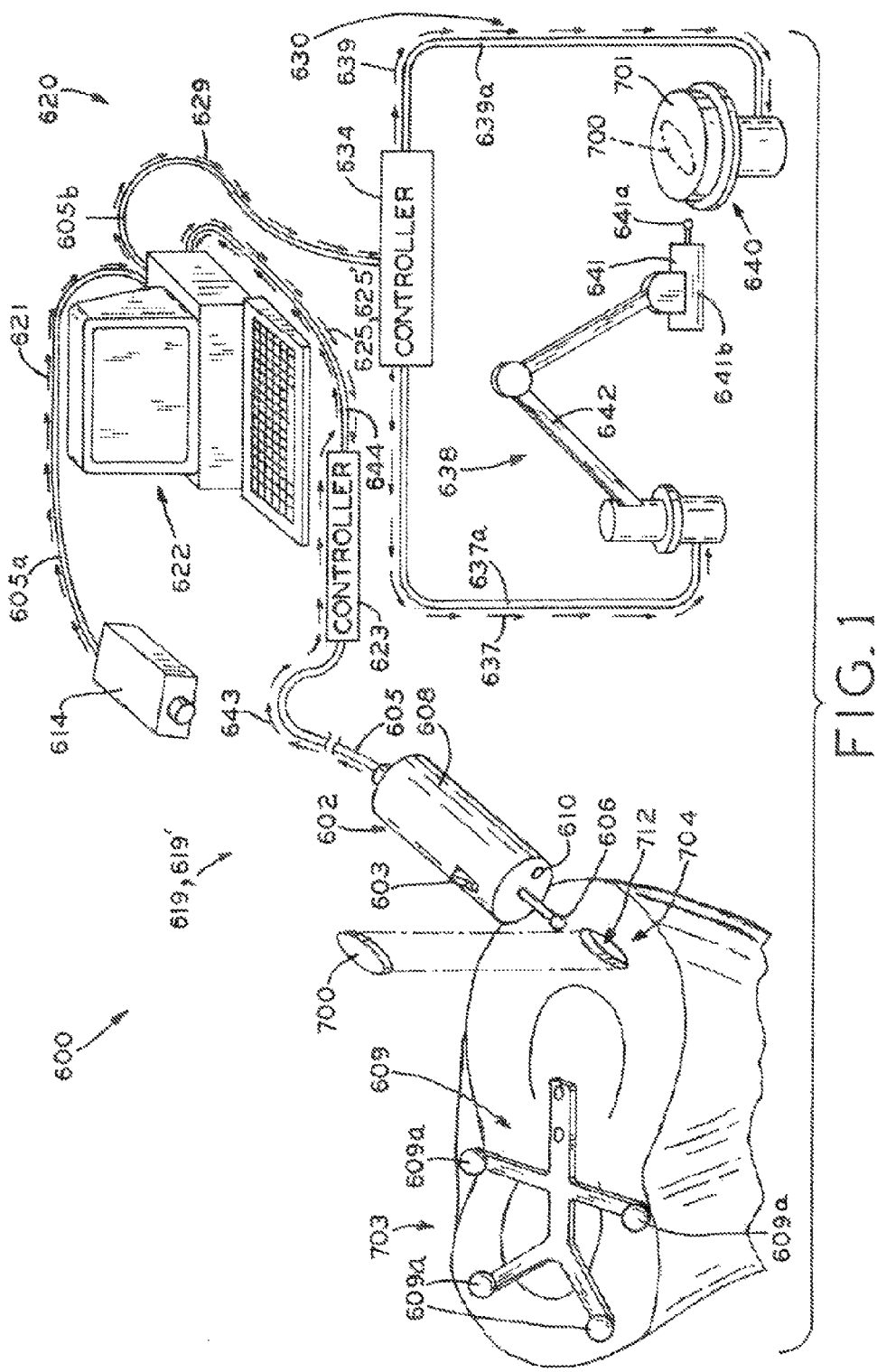
FIG. 1 is a perspective view of an embodiment of an orthopaedic system in accordance with the present disclosure, illustrating a custom implant formed to fit an irregularly shaped void.

Referring to FIG. 1, orthopaedic system 600 includes tracked tissue resection tool 602, tracking system 619, signal conversion system 620, and custom implant forming system 630. As resection tool 602 is used to resect defective tissue 702 (FIG. 2a), tracking system 619 monitors the movement of tool 602. Data points indicative of the monitored cutter position are collected throughout the resection, rendering a set or "cloud" of data points bounding a virtual volume that is representative of void 712. Tracking system 619 sends this data set to signal conversion system 620, which in turn converts the data into implant forming commands 629. Implant forming commands 629 are then sent to implant forming system 630, which creates custom implant 700 sized and shaped to fill void 712 created by the resection of defective tissue 702.

In the illustrated embodiment, orthopaedic system 600 is used to repair defect 702 (FIG. 2a) located in tissue 704 at the proximal end of tibia 703. However, it is contemplated that orthopaedic system 600 may be used to repair other types of tissue, such as bone and non-articular forms of cartilage (such as elastic and fibro cartilage), and may be used for other anatomical surfaces, including but not limited to surfaces associated with the femur, distal tibia, pelvis, talus, glenoid, or humerus, for example.

Referring still to FIG. 1, tissue resection tool 602 includes an operative end adapted to resect tissue, shown as mill 606. Mill 606 is rotatably driven by power transmitted from a remote power source (i.e., an electrical outlet or compressed air reservoir, not shown) via power transmission cable 605. Trigger 603 controls the delivery of power to mill 606. Resection tool 602 can be said to be a "freehand" cutting tool, in that an operator can hold and maneuver handle 608 while manipulating trigger 603 to selectively resect defective tissue 702 (FIG. 2a) in a freehand manner, as described in detail below. An exemplary cutting instrument suitable for use with the present system is described in U.S. Pat. No. 6,757,582, entitled METHODS AND SYSTEMS TO CONTROL A SHAPING TOOL, the entire disclosure of which is hereby expressly incorporated herein by reference.

Referring to FIGS. 4a and 4b, tissue resection tools 602a, 602b, are hand-held instruments similar to tissue resection tool 602, but have alternative operative ends. Tissue resection tool 602a of FIG. 4a includes oscillating blade 606a, while resection tool 602b of FIG. 4b includes scalpel 606b. Moreover, it is contemplated that the operative end of resection tool 602 may be any cutting tool or device capable of excising a quantity of tissue from an anatomical surface, such as a retractable blade, a particulate stream, a cautery device, a rotary cutting blade, a cartilage punch, or an ultrasonic cutting device, for example.

In an exemplary embodiment, tissue resection tool 602 may be modularly adaptable for use with any number of different operative ends. As noted below, an operative end (such as mill 606) of resection tool 602 is in a known spatial relationship with tool positional marker 610, which allows the spatial position and orientation of the operative end to be monitored. When an alternative operative end having a differing geometry replaces mill 606, orthopaedic system 600 is adjusted to account for this new geometry. To effect such adjustment, the user may input identifying information for the new operative end into computer 622, such as by selecting from a pre-programmed list of known operative ends (i.e., "mill," "oscillating blade" or "scalpel"). Specific geometrical and spatial geometry information for each operative end is programmed into computer 622, which in turn allows orthopaedic system 600 to account for any spatial differences between tool positional marker 610 and respective operative ends (i.e., operative ends 606, 606a, 606b). In another example, operative ends 606, 606a, 606b may each include a unique identifier readable by resection tool 602, such as a barcode, radio frequency identification (RFID) tag, or magnet. When one of operative ends 606, 606a, 606b is installed onto resection tool 602, this identifier is sent to computer 622 automatically (i.e., via wireless transmission), obviating the need for the system user to input the information manually.

Although tissue resection tools 602, 602a, 602b are described and depicted herein as hand-held instruments suitable for freehand resections, alternate non hand-held embodiments of resection tool 602 are also contemplated. For example, computer-controlled or haptic robotic arms may be used in conjunction with the present system, such as the system described in U.S. patent application Ser. No. 11/610,728, filed Dec. 14, 2006, entitled IMAGELESS ROBOTIZED DEVICE AND METHOD FOR SURGICAL TOOL GUIDANCE, and commonly assigned with the present application, the entire disclosure of which is hereby expressly incorporated herein by reference.

Referring again to FIG. 1, orthopaedic system 600 further includes tracking system 619 for monitoring the position, orientation and movement of resection tool 602 within a tracked surgical space. In an exemplary embodiment, tracking system 619 includes one or more resection tool positional markers 610 and detector 614, which cooperate to generate data indicative of the position and orientation of mill 606 within a field of view of detector 614, as described below. Although a single detector 614 is shown in FIG. 1 for simplicity, it is contemplated that multiple-detector systems may be used to monitor the surgical space.

Figure 7:
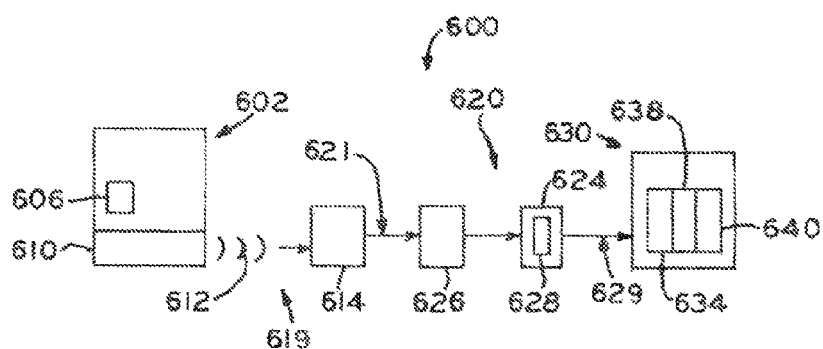
FIG. 7 is a schematic view of an exemplary tracked cartilage repair system in accordance with the present disclosure.

Turning now to FIG. 7, an embodiment of tracking system 619 which monitors the position and orientation of resection tool 602 is schematically depicted. Resection tool positional marker 610 is coupled to resection tool 602, such that the position of mill 606 is in a known (i.e., fixed or calculable) spatial relationship with marker 610. During excision of a target volume, such as the material surrounding and including tissue defect 702 (FIG. 2*a*), detector 614 receives signals 612 emanating from positional marker 610, and each received signal 612 provides a discrete parcel of data indicative of the position and orientation of mill 606. One exemplary detector suitable for use with the present system is the POLARIS SPECTRA brand optical tracking system, which is produced by Northern Digital Inc., of Ontario, Canada (POLARIS SPECTRA is a registered trademark of Northern Digital Inc.). Because positional marker 610 internally generates and distributes signal 612 to detector 614, tracking system 619 may be said to use an active data collection modality. Examples of internally generated signals 612 suitable for use with orthopaedic system 600 include visible light (e.g., light emitting diodes), fluoroscopic, infrared, radio frequency, electromagnetic, or ultrasonic forms of signals, and the like. In exemplary embodiments, internally generated signals may come from accelerometers, gyroscope-based sensors, inclinometers, and other signal generation devices described in U.S. patent application Ser. No. 12/410,884, filed. Mar. 25, 2009 and entitled METHOD AND SYSTEM FOR PLANNING/GUIDING ALTERATIONS TO A BONE, and in U.S. patent application Ser. No. 12/410,854, filed Mar. 25, 2009 and entitled TRACKING SYSTEM AND METHOD, the entire disclosures of which are hereby incorporated herein by reference.

When using tracking system 619 as depicted in FIG. 7, movements of resection tool 602 are monitored by detector 614, and recordation of such movements generates a set of data points representative of a volume of resected material. The data points, which are clustered together within a virtual volume, can be said for form a "cloud" of data points as noted above. At the beginning of resection of defective tissue 702, a first data point collected at a first three-dimensional coordinate can be said to represent a starting point of resection tool 602. As defective tissue 702 is resected to create void 712, subsequent data points collected at subsequent three-dimensional coordinates can be said to represent a corresponding movement of resection tool 602. As a multitude of data points is collected, the data points will combine to define a three-dimensional volume which contains or is tangent to every collected, data point. This three-dimensional volume defined by the "cloud" of data points has a shape and size that mimics the three-dimensional volume of void 712. As described below, this set or cloud of data points is subsequently used to create custom implant 700 such that implant 700 is sized and shaped to correspond to void 712.

Figure 8:
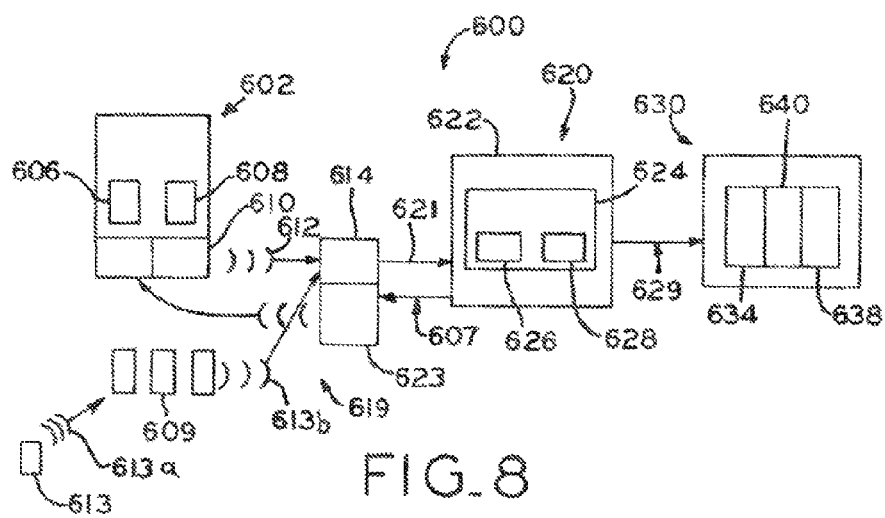
FIG. 8 is a is a schematic view of another exemplary tracked cartilage repair system in accordance with the present disclosure.

In addition to positional marker 610 fixed to resection tool 602, tracking system 619 may include tibia position markers 609 (FIG. 1) fixed to tibia 703. Referring to FIG. 8, an embodiment of the orthopaedic system 600 in which tracking system 619 monitors the positions of both tibia 703 and resection tool 602 is schematically illustrated. As described in detail below, the addition of tibial position monitoring allows movement of tibia 703 during the surgical procedure while preserving the ability to collect comprehensive and accurate data regarding the volumetric characteristics of void 712 (FIG. 1) formed during resection of defective tissue 702 (FIG. 2*a*).

As described above with respect to the configuration of tracking system 619 shown in FIG. 7, a set or cloud of data points is created during resection of defective tissue 702. However, if tibia 703 moves during this resection, defective tissue 702 and resection tool 602 move also. If such movement is not accounted for, the three-dimensional coordinates of a data point collected before the movement will fail to properly correspond with the three-dimensional coordinates of a data point collected after the movement because the latter data point will be spaced from the former data point not only by the amount of movement of resection tool 602, but also by the amount of movement of tibia 703. Tracking the movement of tibia 703, on the other hand, allows the vector associated with a given movement of tibia 703 at a given time to be subtracted from the vector associated with the movement of resection tool 602 at the same time, thereby correcting for tibial movement and keeping the integrity of the data cloud intact.

In the illustrative embodiment of FIG. 2*a*, tibia position marker 609 includes an array of fiducials 609*a*, which are collectively fixed to tibia 703 in a known (i.e., fixed or calculable) spatial relationship with tissue defect 702. External signal generator 613 (FIG. 8) generates controller ambient signal 613*a* in the tracked surgical space, and fiducials 609*a* reflect ambient signal 613*a* to produce reflected signal 613*b*. As shown in FIG. 2*a*, position marker 609 includes four fiducials 609*a* arranged in a generally planar configuration. The individual point signals emanating from each of the four fiducials 609*a* define a planar quadrilateral shape, the position and orientation of which can be determined within the tracked surgical space. By contrast, a single point signal can show movement but not changes in orientation. Thus, reflected signal 613*b* emanating from positional marker 609 is indicative of the position and orientation of tibia 703 (and, thus, of tissue defect 702). Movement of tibia 703 is monitored by detector 614 in a similar manner as discussed above with respect to the monitored movement of resection tool 602.

Because emanation of signal 613*b* from tibia positional marker 609 is accomplished by passively reflecting the externally generated ambient signal 613*a*, tracking system 619 as depicted in FIG. 8 may be said to use a passive data collection modality in addition to the active data collection described above. Externally generated, ambient signal 613*a* can be any signal capable of creating a reflected signal 613*b* that is uniquely distinguishable from ambient signal 613*a* by detector 614. For example, ambient signal 613*a* may be altered to produce reflected signal 613*b* by a change in frequency, wavelength, or shape of ambient signal 613*a*, or by redirection of less than all of ambient signal 613*a*. Exemplary systems and methods for passive data collection are described in U.S. patent application Ser. Nos. 12/410,854 and 12/410,884, incorporated by reference above.

Figure 9:
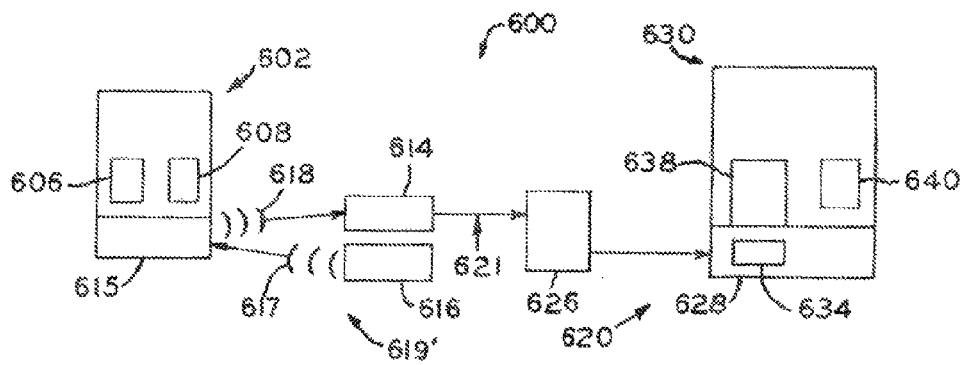
FIG. 9 is a schematic view of yet another exempla tracked cartilage repair system in accordance with the present disclosure.

It is contemplated that positional tracking and the associated acquisition of data for one or both of tibia 703 and resection tool 602 may be accomplished using any combination of active data collection and passive data collection. For example, FIG. 9 schematically illustrates orthopaedic system 600 having tracking system 619', which utilizes only passive data collection for collection of data indicative of the position and orientation of mill 606 of resection tool 602. In the depicted embodiment, tracking system 619' includes signal generator 616 which generates ambient signal 617, and further includes passive tool position marker 615 which is coupled to resection tool 602 in a known (i.e., fixed or calculable) spatial relationship to mill 606. Passive tool position marker 615 is generally analogous to tibia position marker 609, which includes an array of fiducials 609*a* as described above. However, passive tool position marker 615 is fixed to resection tool 602 rather than tibia 703. Upon interacting with passive tool position marker 615, ambient signal 617 is altered and transmitted to detector 614 as reflected signal 618.

Signal generator 616, ambient signal 617 and reflected signal 618 are generally analogous to generator 613, ambient signal 613a and reflected signal 613b, discussed above, except for being adapted for use with resection tool 602 rather than tibia 703.

Other embodiments of tracking system 619 are contemplated, including systems utilizing any combination of active and passive data collection for acquiring: data associated with mill 606 of resection tool 602 and/or tibia 703. For example, a "fully passive" system may include a combination of passive marker 609 (FIGS. 1, 2a and 8) affixed to tibia 703, passive tool position marker 615 (FIG. 9) coupled to resection tool 602, and one or both of signal generators 613, 616 (FIGS. 8 and 9). Passive markers 609, 615 may reflect one or more ambient signals (i.e., signals 613a, 617) to create distinct reflected signals 613b, 618 that are distinguishable from one another by detector 614, or by separate individual detectors.

Detector 614 thus receives any number of reflected or generated signals from the monitored surgical space, as described above. Turning again to FIG. 1, these aggregated received signals pass from detector 614 to computer 622 via data input cable 605a as detected signal 621 (FIGS. 7-9). Detected signal 621 is received by signal conversion system 620, which may include components for storage, conversion and distribution of detected signal 621 as described below. As illustrated, detected signal 621 represents any combination of signals 612, 613a, 613b and 618. As such, detected signal 621 includes data associated with movements of mill 606 of resection tool 602 and/or tibia 703 within the surgical space monitored by detector 614.

Tracking system 619 may be calibrated in order to facilitate or enhance receipt and/or processing of detected signal 621. In one exemplary embodiment, such calibration is performed by providing signal conversion system 620 with information related to orthopaedic system 600 and the surrounding environment, including the spatial relationship between mill 606 and tool positional marker 610 in resection tool 602, functional characteristics of mill 606, the location and/or orientation of markers 609, and/or dimensional and positional information related to tibia 703, tissue defect 702, or other anatomical structures. Calibration of tracking system 619 may be accomplished through any suitable system and method, such as by an optically tracked pointer, video or camera imaging, manual information entry, and/or operator performance of specific commands. Where calibration methods are utilized, calibration can be performed regardless of whether tracking system 619 uses active data collection, passive data collection, or a combination of both.

Referring now to FIG. 8, an exemplary embodiment of signal conversion system 620 is shown schematically. Signal conversion system 620 includes computer 622 (described above) having processor 624 which has access to data storage device or memory 626 containing conversion software 628. In the exemplary embodiment of FIG. 1, computer 622 is a stand-alone computing device. Exemplary stand alone computing devices include a general purpose computer, such as a desktop computer, a laptop computer, and a tablet computer smartphone, handheld computing device, or other suitable computing devices. Although computer 622 is illustrated as a single computing system, it should be understood that multiple computing systems may be used together, such as over a network or other methods of transferring data.

In one embodiment, computer 6 may be attached to the surgical table rails of a table supporting the patient, so that computer 622 may be both physically small and within the immediate viewing space of the surgeon. When computer 622 is within the surgeon's grasp, interaction with a graphical user interface of computer 622 may be accomplished with a touch screen or mechanical switches which are engaged by the surgeon or a nurse. In one embodiment, the surgeon or nurse interacts with computer 622 through voice commands received by a microphone associated with the computing system. The computing system may be able to identify the voice of the surgeon or other authorized user. In one embodiment, the surgeon or nurse interacts with the computing system through gestures captured by detector 614. In any of the discussed embodiments, computer 622 or at least a display portion of computer 622 may be contained within a bag or other sterilization mechanism and the surgeon or other authorized user interacts with the computing system through the bag or other sterilization mechanism.

Memory 626 is a computer readable medium and may be a single storage device or may include multiple storage devices, located either locally with computer 622 or accessible across a network. Computer-readable media may be any available media that may be accessed by processor 624 of computer 622, and includes both volatile and non-volatile media. Further, computer readable-media may be one or both of removable and non-removable media. By way of example, computer-readable media may include, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which may be used to store the desired information and which may be accessed by computer 622.

Computer 622, in addition to containing the specialized instructions for orthopaedic system 600 embodied in conversion software 628, may also include operating system software (not shown). An exemplary operating system software is a WINDOWS operating system available from Microsoft Corporation of Redmond, Wash. Computer 622 may further include communications software (not shown) which allows computer 622 to communicate with one or more computer networks, such as a local area network, a wide area network, a public switched network, any type of wired network, any type of wireless network, and combinations thereof. An exemplary public switched network is the Internet. Exemplary communications software includes browser software, and other types of software which permit computer 622 to communicate with other devices across a network. In one embodiment, computer 622 also communicates with one or more additional computing devices (not shown) over a network, such as remote computing devices forming part of a hospital network or surgery center network.

In use, and as illustrated in FIG. 8, processor 624 of computer 622 receives detected signal 621 and executes instructions of conversion software 628 to convert detected signal 621 into data indicative of the location, orientation, and movement of mill 606 of resection tool 602. If tibia 703 is also being tracked, comparable data is converted in similar fashion. The converted data is output to memory 626, where it is stored for further access by conversion software 628.

When executed by processor 624, conversion software 628 accesses the stored raw data collected by detector 614 and compiled in memory 626, and creates a virtual three-dimensional volume from the individual data points. This virtual three-dimensional volume represents the same volumetric size, shape and boundaries defined by the data set or "cloud" of data points discussed above. Software and systems for removing erroneous and/or outlier data may also be provided, to smooth the virtual "surface" of the cloud, of data points. Methods for such smoothing include computation of a non-uniform rational B-spline (NURBS) approximation of the virtual surface. Alternatively, a 3D lowpass filter may be utilized to exclude outliers data points and smooth the virtual surface.

The virtual volume is translated into a series of implant forming commands 629, which are instructions (i.e., machine-language instructions) for the manufacture of custom implant 700 by custom implant forming system 630 (FIG. 1). These instructions provide an input to implant forming: system 630 to create implant 700 with the same or analogous volumetric characteristics exhibited by the virtual volume, and therefore by void 712.

Although implant forming system 630 is described and shown herein as being a system in the vicinity of orthopaedic system 600, it is also contemplated that implant forming system may be remote. For example, implant forming commands 629 may be transmitted to a remote to an implant forming facility (i.e., via a computer network as discussed above), which may rapidly produce and deliver custom implant 700 to the surgical site. Exemplary "made-to-order" systems and methods that may be adapted for use with the present disclosure are disclosed in U.S. Provisional Patent Application Ser. No. 61/324,525, filed Apr. 15, 2010 and entitled METHODS OF ORDERING AN MANUFACTURING ORTHOPEDIC COMPONENTS, which is commonly assigned with the present application, the entire disclosure of which is hereby expressly incorporated by reference herein.

Memory 626 can continuously aggregate and store data derived from detected signal 621 as such data is received. Such storage allows the user of orthopaedic system 600 to release the aggregated data to conversion software 628 when appropriate, i.e., when the data forms a complete volumetric representation of void 712 after void 712 is completely formed. Thus, implant forming system 630 can begin generation of implant 700 at any time after the final shape and size of void 712 is determined.

It is also contemplated that the multiple functions performed by computer 622 may be performed by stand-alone components, or these functions may be integrated into other parts of orthopaedic system 600. Referring to signal conversion system 620 as schematically depicted in FIG. 7, for example, detected signal 621 is sent directly to a stand-alone memory 626 to be stored as raw data, and is subsequently accessed by conversion software 628 programmed into a stand-alone processor 624 to generate implant forming commands 629. Exemplary stand-alone memory systems include USB storage devices, external CD or DVD drives, and the like. In the configuration shown in FIG. 9 signal conversion system 620 includes a stand-alone memory 626 but integrates conversion software 628 into controller 634 of implant forming system 630. Other permutations of conversion system 620 may be used, as required or desired for a particular application.

In the embodiment of FIG. 1, implant forming commands 629 are transmitted from computer 622 to controller 634 via data output cable 605b. Controller 634 separates implant forming commands 629 into cutter commands 637 thr implant cutter assembly 638 and implant rotation commands 639 for turntable 640. Controller 634 distributes commands 637, 639 to their respective hardware destinations via data command transfer cables 637a, 639a respectively. In this way, controller 634 utilizes custom implant forming commands 629 to direct interactions between implant cutter assembly 638 and turntable 640, which has implant blank 701 (i.e., a standard-sized allograft plug or a synthetic plug) mounted thereto (FIG. 1).

Under such directed interaction between implant cutter assembly 638 and implant blank 701, custom implant forming system 630 manufactures custom implant 700 from implant blank 701, such that custom implant 700 replicates the volumetric representation of void 712 stored as data points in memory 626. With implant blank 701 fixed to turntable 640, cutter 641 (shown as mill 641a driven by motor 641b) advances toward blank 701 by articulation of robot arm 642, which is capable of moving cutter 641 through multiple degrees of freedom, such as six degrees of freedom. A designated portion of implant blank 701 is milled away by cutter 641 according to cutter commands 637. When such designated portion of the material of implant blank 701 has been fully removed, turntable 640 rotates implant blank 701 according to rotation commands 639, thereby presenting a new portion of implant blank 701 to cutter 641. Cutter 641 then mills away a second designated portion in similar fashion to the first milling operation. This mill-rotate-mill progression is iteratively repeated until all designated portions of implant blank 701 have been removed from the side and/or top of implant blank 701, leaving finished custom implant 700.

Figure 3:
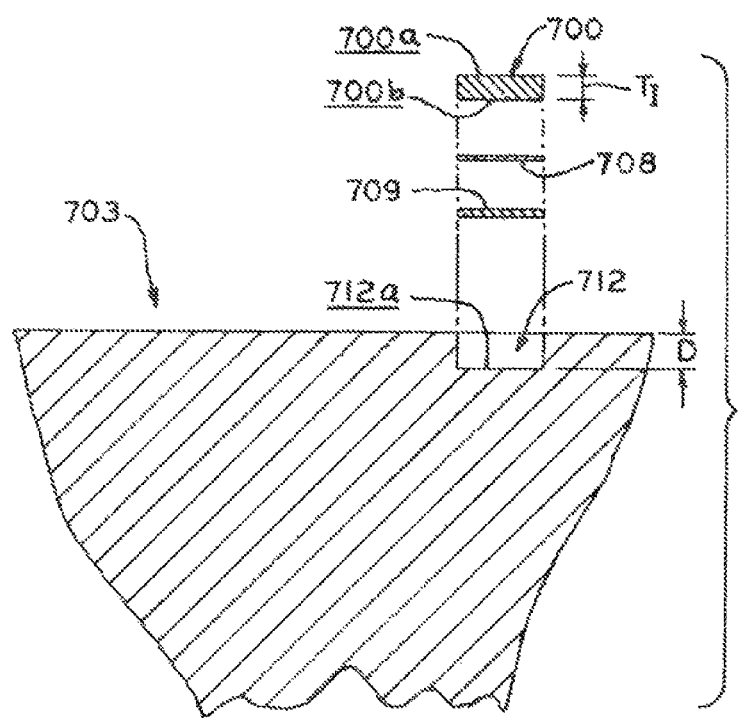
FIG. 3 is an elevation, section view of the proximal tibia shown in FIG. 2a, illustrating a custom implant and optional shims.

It is also contemplated that material removal from the bottom face of implant blank 701 may be accomplished by re-mounting, implant blank 701 to turntable 640 to present such bottom face to cutter 641. In an exemplary embodiment, however, the top and bottom faces of implant blank 701 may be left undisturbed by cutter 641 to fit a void 712 having a particular, preset resection depth D (FIG. 3). As noted below, leaving the top and bottom faces of implant blank 701 undisturbed allows any special finishes on articular surface 700a and bone-contacting surface 700b of custom implant 700 to remain intact.

While custom implant forming system 630 represents particular embodiment of a computer numerical controlled (CNC) system, other CNC systems may be used, such as laser cutting systems, water jet cutting systems, CNC milling and routing systems, and the like. Examples of exemplary CNC systems include SINUMERIK brand programmable numeric controllers available from Siemens AG of Berlin, Germany (SINUMERIK is a registered trademark of Siemens AG).

However, it is also contemplated that any number of other suitable methods may be used to create custom implant 700 from a raw or blank material, such that implant 700 replicates the resected volume of void 712. For example, custom implant 700 may be generated using a rapid prototyping process, such as three dimensional printing, stereolithography, selective laser sintering, fused deposition modeling, laminated object manufacturing, or electron beam melting, for example.

Once created, the shape and profile of implant 700 mimics void 712 created previously by the resection process described above. For example, custom implant 700 is illustrated in FIGS. 1 and 2b as being generally oval in shape, in order to accommodate a correspondingly elongate, oval-shaped resection void 712 (FIG. 1). Resection void 712 represents an appropriate resection for the elongate nature of tissue defect 702 (FIG. 2a). However, custom implant 700 may take any shape associated with the movements or functions of mill 606 as represented by the volumetric data conveyed in detected signal 621.

As it is described above, orthopaedic system 600 is capable of forming custom implant 700 based on the shape and volumetric characteristics of void 712, regardless of whether void 712 is irregularly shaped. This allows a surgeon to create void 712 in a freehand manner, thereby allowing the surgeon flexibility in pursuing the surgical goal removal as little of the healthy tissue surrounding defect 702 as practical. The freehand resection technique enabled by orthopaedic system 600 is particularly advantageous for elongated or irregular defects such as defect 702 (FIG. 2*a*). Orthopaedic system 600 can be used to create custom implant 700 closely matching the original profile of defect 702. By contrast, making a cylindrical resection 800 to fit a pre-made cylindrical plug can result in removal of a larger proportion of healthy tissue, as illustrated in FIG. 2*b*. In addition, the freehand technique may reduce the surgical time requirements, as orthopaedic system 600 obviates the need for multiple standard-size plugs used in some mosaicplasty systems and methods. In addition, orthopaedic system 600 may monitor the shape of void 712 during resection of defective tissue 702 to avoid an undercut (i.e., a situation in which resection depth D is too small) during a freehand resection. In one exemplary embodiment, the shape and volumetric characteristics of void 712 may be graphically displayed to a surgeon during the resection of defective tissue 702, including desired resection depth D. The display can indicate where further material removal is necessary to avoid and undercut situation. Avoiding an overcut (i.e., a situation in which resection depth D is too large) can be accomplished as described in detail below.

However, it is contemplated that some constraints may be placed on the otherwise freehand resection method for creatin void 712. Referring to FIG. 3, for example, resection depth D of void 712 may be set to a particular desired value, such as to accommodate custom implant 700 having a given thickness $T_I$ while avoiding any resurfacing of articular surface 700*a* or bone-contacting surface 700*b* (resurfacing of custom implant 700 is described in detail below). Where depth D is greater than thickness $T_I$, such as where defective tissue 702 is found to extend more deeply into tibia 703 than can be accommodated by thickness $T_I$, implant spacers 708, 709 (FIG. 3) may be disposed between bone-contacting surface 700*b* of implant 700 and the lower resected surface 712*a* of void 712 to bring articular surface to a desired elevation. As illustrated in FIG. 3, a kit including multiple implant spacers 708, 709 of varying thickness, i.e. thin implant spacer 708 and thick implant spacer 709, may be provided to offer a wide variety of total implant thicknesses to the surgeon. In an exemplary embodiment, spacers 708, 709 may be made of a porous bone-ingrowth material.

In order to facilitate the use of resection tool 602 for the creation of void 712 having a particular, predefined depth D, signal conversion system 620 may collect data regarding the operational status of resection tool 602, such as whether resection tool 602 is on or off, how much power is flowing to mill 606 (i.e., the "load state"), etc. This raw data is collected by tool controller 623 (FIG. 1), which in turn transmits signal 643 via data transmission cable 644 to signal computer 622. It is also contemplated that signal 643 may pass directly from resection tool 602 to computer 622. Each parcel of data carried by signal 643 may be time-stamped by signal conversion system 620 to correspond with correspondingly time-stamped data regarding the location and orientation of mill 606, described in detail above.

Signal conversion system 620 processes signal 643 in a similar fashion to detected signal 621, which then relays the processed signal back to controller 623 as anatomical shaping commands 625. In an exemplary embodiment, conversion software 628 iteratively computes the depth of void 712 throughout the resection operation, and compares such computed depth to the pre-defined desired resection depth D (which may be created as part of a pre-surgical plan and stored in memory 626). If comparison of detected signal 621 indicates mill 606 of resection tool 602 is at or near a position that violates the pre-defined resection depth D, then signal conversion system 620 issues an appropriate anatomical shaping command 625 to resection tool controller 623, such as a command to cut power to resection tool 602 or some visual, audio, or tactile indicator, such as an audible alarm. Where power to resection tool 602 is cut in response to anatomical shaping command 625, signal conversion system 620 may require the operator to provide some form of user feedback to resection tool controller 623 as a condition for restoring power to mill 606. An exemplary system for use in the generation of anatomical shaping commands to control a cutting instrument is described in U.S. Pat. No. 6,757,582, entitled METHODS AND SYSTEMS TO CONTROL A SHAPING TOOL, incorporated by reference above.

Resection depth D is described above as an exemplary predefined volumetric parameter of void 712. Advantageously, constraining depth D allows surfaces 700*a*, 700*b* of custom implant 700 to remain undisturbed, thereby keeping any special articular or bone-contacting surface characteristics intact. For example, articular surface 700*a* may be lubricious and/or smooth to facilitate articulation with an adjacent joint surface a femoral condyle), while bone-contacting surface 700*b* may be porous or roughened to facilitate bone ingrowth. However, it is contemplated that boundaries of other desired volumetric characteristics of void 712 may be established and programmed into controller 623, and violations of these boundaries may be prevented in the similar fashion as depth D described above.

Implant 700 may be used with a void 712 having resection depth D that is greater than implant thickness $T_I$ by utilizing one or more of spacers 708, 709 as noted above. Implant 700 may be also used with a void 712 having a shallower depth D than implant thickness $T_I$ by shaping articular surface 700*a* after implantation. For example, resection tool 602 may be used to mill an elevated portion of custom implant 700, such that the finished shape and contour of articular surface 700*a* corresponds with the original contour of tissue 704 (FIG. 1), as described in detail below.

In addition to generating anatomical shaping commands 625 as described above, computer 622 may manipulate resection tool 602 via resection tool controller 623 for reasons other than creation of void 712. For example, controller 623 may be ordered to shut down resection tool 602 when mill 606 moves out of the surgical space monitored by detector 614, or if aberrant power inputs are detected, or after a fixed elapse of time.

As an alternative to controlling resection tolerances via orthopaedic system 600, as described above, resection tolerances may instead be controlled by the use of cut guides or templates. For example, a cut guide (not shown) with a channel may be placed upon tibia 703 over tissue defect 702, and may physically prevent mill 606 from extending past a particular defined resection depth D (such as by allowing mill 606 to pass through the channel, but not handle 608). Other cut guide and template arrangements may be used or adapted for use with the present disclosure. One exemplary system and method for using a cut guide to control resection depth is disclosed in U.S. Pat. No. 7,794,462, filed Mar. 19, 2007, entitled HANDPIECE CALIBRATION DEVICE, and commonly assigned with the present application, the entire disclosure of which is hereby expressly incorporated by reference.

In addition to collecting data associated with the movements and/or functions of resection tool 602, surface contour information relating to tissue 704 (FIG. 1), which surrounds and includes defective tissue 702, may be collected prior to excising defective tissue 702. Collection of surface contour information of tissue 704 may be accomplished through any suitable method, including the use of an optically tracked pointer (not shown), video or camera imaging (not shown), and algorithmic extrapolation from information provided by markers 609 (FIG. 1). One exemplary embodiment of surface contour collection systems and methods may be found in U.S. patent application Ser. No. 12/191,129, filed Aug. 14, 2008, entitled METHOD OF DETERMINING A CONTOUR OF AN ANATOMICAL STRUCTURE AND SELECTING AN ORTHOPAEDIC IMPLANT TO REPLICATE THE ANATOMICAL STRUCTURE, and commonly assigned with the present application, the entirety of which is hereby expressly incorporated herein by reference.

According to one embodiment of orthopaedic system 600, custom implant 700 is manufactured by implant forming system 630 to replicate not only the size and shape of void 712 (as described in detail above), but also the original surface contour of tissue 704. In this embodiment, conversion software 628 creates custom forming commands 629 from both the acquired data set generated during excision of defective tissue 702, as well as collected surface contour information. Custom implant forming system 630 utilizes custom implant forming commands 629, which incorporate such surface contour information, to manufacture custom implant 700 to be sized to correspond with the size and shape of void 712 and the contour of tissue 704.

In yet another configuration, orthopaedic system 600 may allow a surgeon to replicate the original surface contour of tissue 704 by "freehand" milling of articular surface 700a of custom implant 700 after implantation. This method is described, in detail below in the context of exemplary surgical methods 650, 660.

Figure 5:
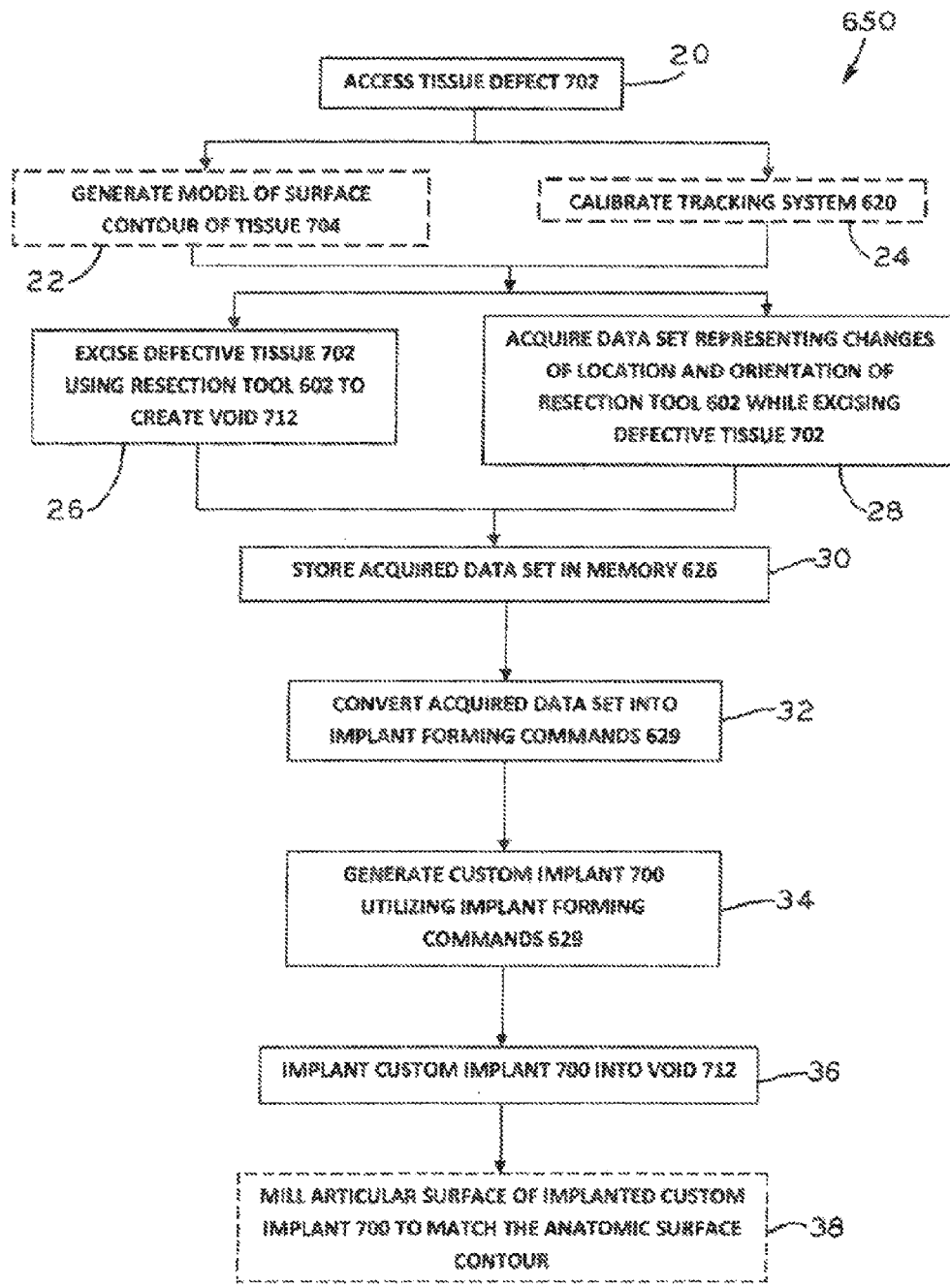
FIG. 5 is a flow chart of an exemplary method of the present disclosure.

Referring now to FIG. 5, an exemplary method of utilizing orthopaedic system 600 is presented as method 650. The surgeon begins method 650 by accessing defective tissue 702, using any suitable surgical method including tissue retraction or minimally invasive surgical techniques, at step 20.

With defective tissue 702 thus exposed, surface contour information relating to tissue 704 surrounding and including defective tissue 702 may be collected at step 22. Step 22 is represented by dashed lines in FIG. 5 to indicate that collection of surface contour information may not be performed, depending on the particular embodiment of orthopaedic system 600 in use and surgeon preference. As described in detail herein, collected surface contour information may be used in conjunction with orthopaedic system 600 to replicate the anatomical surface contour the healthy tissue surrounding defective tissue 702 after implantation of custom implant 700. An exemplary method and system for collecting surface contour of an anatomical surface is disclosed in U.S. patent application Ser. No. 12/191,429, entitled METHOD OF DETERMINING A CONTOUR OF AN ANATOMICAL STRUCTURE AND SELECTING AN ORTHOPAEDIC IMPLANT TO REPLICATE THE ANATOMICAL STRUCTURE incorporated herein by reference above.

With reference to step 24 shown in FIG. 5, calibration of tracking system 619 may be performed as described above. While exemplary method 650 depicts calibration of tracking system 619 as occurring after defective tissue 702 is accessed, methods of utilizing orthopaedic system 600 are possible in which any required calibration of signal conversion system 620 may occur prior to accessing defective tissue 702. Moreover, calibration step 24 is shown in dashed lines to indicate that this step may be eliminated from method 650 as required or desired for a particular application.

Next, excision step 26 and data acquisition step 28 of exemplary method 650 are performed. In steps 26, 28, the surgeon excises tissue defect 702 while contemporaneously acquiring information (such as data associated with movements or functions of mill 606) relating to resection tool 602. In order to create an accurate cloud or set of data points, data associated with mere movement of resection tool 602 (i.e., when mill 606 is not in contact with any portion of tibia 703) is distinguished from data associated with the actual excision of tissue defect 702. The surgeon may manually provide this data by providing input to orthopaedic system 600 (i.e., via a button or foot pedal) to start and stop data collection. Alternatively, the load state of mill 606 may be measured and used to determine when mill 606 is being used to resect tissue. Where the load state is used for this purpose, resection tool 602 may be calibrated or "taught" the difference between a tissue-resection load state and a free-spinning load state by using resection tool in a controlled environment and correlating collected load state data with the known status i.e., cutting or not cutting) of mill 606.

Yet another option is to collect surface contour information, as described in detail above, and to register this surface contour information to tibia position marker 609, so that the outer boundaries of tissue 704 are known within memory 626 of computer 622. Then, when mill 606 is observed by detector 614 passing this calculated outer bound towards tibia 703, data points are collected and recorded. Conversely, if mill 606 moved past the outer boundary away from tibia 703, collection and recordation of data points ceases.

As represented in steps 30 and 32, the acquired data set (at step 28) relating to resection tool 602 is stored in memory 626 (step 30) of signal conversion system 620 (FIGS. 1 and 7-9) and converted at step 32 into implant forming commands 629 by conversion software 628 (FIGS. 7-9). In step 34, implant forming commands 629, are used by custom implant forming system 630 (FIGS. 1 and 7-9) to generate custom implant 700, as discussed above.

With void 712 created and custom implant 700 generated, custom implant 700 is then implanted into void 712. Because custom implant 700 corresponds in size and shape to void 712, implant 700 forms a close, custom fit within void 712. However, a surgeon may perform minor reshaping of implant 700 and/or void 712 to further refine the fit therebetween.

Optionally, if articular surface 700a of implant 700 is elevated above the surrounding bone of tibia 703, articular surface 700a may be milled at step 38 to replicate the original contour of tissue 704 in the manner described above. To ensure that this milling creates an articular surface comparable or identical to the original anatomic curvature, implant resurfacing commands 625' (FIG. 1) may be issued to resection tool controller 623 in a similar manner as anatomical shaping commands 625, described above. However, rather than preventing mill 606 from exceeding the allowable tolerances of void 712, implant resurfacing commands 625' are adapted to prevent any shaping of articular surface 700a beyond the original surface contour of tissue 704, a virtual model of which was previously generated at step 22.

Surface contour information, collected prior to excising defective tissue 702, is first translated by conversion software 628 into a series of surface contour tolerance values and stored in memory 626. During milling of the elevated portion of articular surface 700a of custom implant 700, computer 622 continuously receives newly detected signals 612, 613a, 613b and 618 (relating to acquired data associated with mill 606 of resection tool 602, as described above) which is simultaneously and continuously converted to detected signal 621. Detected signal 621 is compared to the previously computed surface contour tolerance values by conversion software 628. The results of such comparison indicate whether mill 606 of resection tool 602 is nearing a violation of surface contour tolerance values.

If such violation is imminent, computer 622 provides implant resurfacing command 625' to resection tool controller 623, which in turn causes shutdown of tissue resection tool 602 and/or some visual, audio, or tactile indicator, such as an audible signal to an operator in a similar fashion as described above. One system which may be useable for shaping of articular surface 700a of custom implant 700 is described in U.S. Pat. No. 6,757,582, incorporated by reference above.

Figure 6:
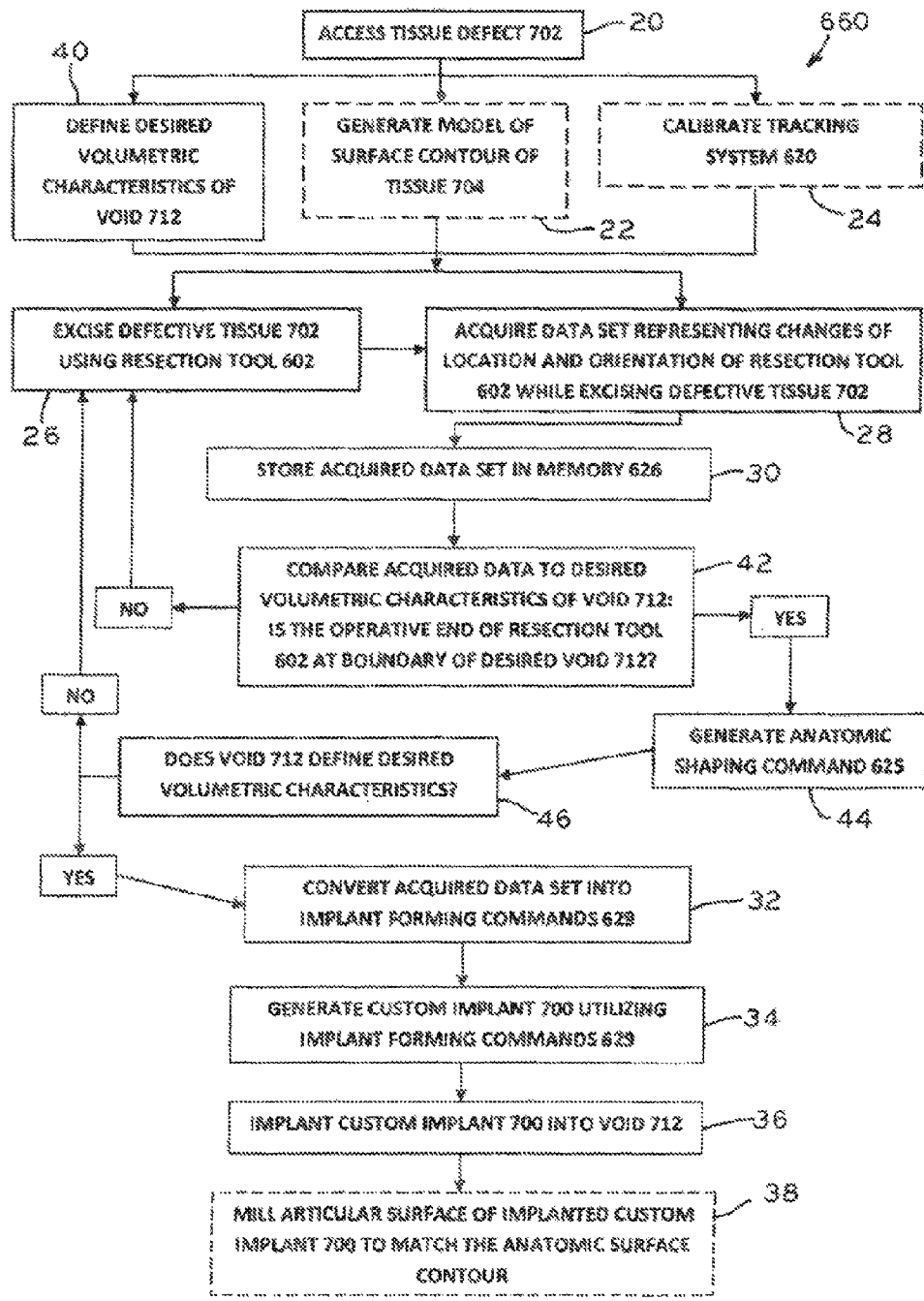
FIG. 6 is a flow chart of another exemplary method of the present disclosure.

An alternative exemplary method of utilizing orthopaedic system 600, described and depicted herein, is presented in FIG. 6 as method 660. Method 660 includes the steps of method 650, but constrains one or more of the boundaries of void 712 to a predefined value (i.e., resection depth D described above) by way of a feedback loop controlling resection tool 602.

After accessing step 20, step 40 is added to define the volumetric characteristics of void 712. In method 650, implant 700 is generated based on void 712 created during excision step 26. In method 660, by contrast, void 712 is itself specified, at least in part, at step 40. While step 40 is shown as occurring after accessing step 20, it is contemplated that step 40 can occur at any time before the completion of excision step 26.

With one or more volumetric characteristics of void 712 (i.e., resection depth D shown in FIG. 3) now defined, excision step 26 and data acquisition and storage steps 28, 30 proceed as described with respect to method 650 (FIG. 5). As the data is stored in step 30, such data is continuously, iteratively compared in step 42 to the boundaries or outer limits of the desired volumetric characteristics of void 712 defined in step 40. If the operative end mill 606 of resection tool 602 is at (or near) this boundary, anatomic shaping command 625 (described in detail above) issues and creates its desired effect, shutting down resection tool 602 or sounding an alarm. If, on the other hand, the boundary comparison step 42 finds that the operative end of resection tool 602 is within the predefined volume of void 712, excision step 26, data acquisition step 28 and data storage step 30 continue.

In some applications, it may be desirable to register tibia 703 and defect 702 to a coordinate system within the tracked surgical space to ensure that void 712 will be properly centered around defect 702 after the excision is complete. In such applications, the comparison at step 42 is not only performed to compare the acquired data points to the volumetric characteristics of void 712, but also compares relative position of the data points to defect 702. Registration can be accomplished by any suitable method, such as by touching mill 606 to the center of defect 70 before excision begins, while tibia 703 is tracked or immobilized (as described above). By recording this position of mill 606 within the monitored surgical space, computer 622 is taught the position of defect 702 within the monitored surgical space. Computer 622 can therefore "register" or overlay the desired volumetric characteristics of void 712 with defect 702, and issue implant forming commands 629 whenever mill 606 is outside of void 712 (and therefore, away from defect 702).

Once anatomic shaping command 625 is generated at step 42, a second inquiry is made at step 46 as to whether void 712 has achieved the desired volumetric characteristics defined in step 40. If the answer to this inquiry is "yes", i.e., if the resected volume of void 712 matches the desired volume, then the acquired data set is converted into implant forming commands 629 and the processes of generating, implanting and (optionally) resurfacing custom implant 700 proceeds as described above with respect to method 650. If, on the other hand, the answer is "no", i.e., the desired resected volume of void 712 has not yet been achieved, method 660 reverts to excision step 26 to continue removing tissue and expanding void 712.

Although orthopaedic system 600 is described herein in the context of creation and implantation of custom implant 700, it is contemplated that pre-formed implants may also be used. For example, the dimensional representations of void 712 may be compared to a library of predefined shapes for which pre-formed implants are available, i.e., a standard conical shape. In one alternative embodiment, if the dimensional representations of the shape of tissue 704 excised are within specified tolerances of the shape of an available pre-formed implant, orthopaedic system 600 may alert the user that a cartilage punch or other standard resection tool corresponding to the predefined shape may be used to create void 712 sized to fit such standard implant. In another alternative, resection tool 602 may be controlled by anatomical shaping commands 625, as described in detail above, to create void 712 corresponding to the shape of a pre-formed implant. Systems relating to the use of a library of implants and methods relating to best-fit analyses may be found in U.S. patent application Ser. No. 12/191,429, entitled METHOD OF DETERMINING A CONTOUR OF AN ANATOMICAL STRUCTURE AND SELECTING AN ORTHOPAEDIC IMPLANT TO REPLICATE THE ANATOMICAL STRUCTURE, incorporated by reference above.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method of repairing a tissue defect in an anatomical structure, the method comprising:
    monitoring removal of a portion of the anatomical structure including monitoring a plurality of movements of a resection tool having an operative end while the operative end resects tissue from the anatomical structure to create a void having a first shape, the portion including the tissue defect;
    determining a second shape corresponding to the first shape of the void including using the plurality of movements to create a plurality of data points defining the second shape, wherein monitoring the plurality of movements includes detecting an emanated signal from a positional marker included in or coupled to the resection tool and wherein the emanated signal is indicative of at least one of a position and an orientation of the operative end; and
    after determining a second shape, providing an implant having the second shape for placement within the void, the second shape generally matching the first shape.

2. The method of claim 1, wherein providing an implant comprises:
    translating the plurality of data points into a plurality of implant forming commands; and
    using the plurality of implant forming commands to form the implant.

3. The method of claim 2, further including monitoring milling an articular surface of the implant to a desired contour after the implant has been implanted.

4. The method of claim 2, in combination with a method of resurfacing the implant, the method of resurfacing comprising:
collecting surface contour information of the anatomical structure before removal of a portion of the anatomical structure, the surface contour information creating a virtual articular surface model;
translating the surface contour information into surface contour tolerance values;
after the implant has been implanted, monitoring a second plurality of movements of the resection tool during removal of a portion of the articular surface, said monitoring creating a location signal representative of a location of the operative end of the resection tool;
iteratively comparing the location signal to the surface contour tolerance values to determine whether the operative end of the resection tool is in violation of the surface contour tolerance values;
generating an implant resurfacing command if the operative end of the resection tool is in violation of the surface contour tolerance values.

5. The method of claim 2, wherein translating the plurality of data points comprises:
transmitting the emanated signal to a memory;
processing the emanated signal to create a virtual three-dimensional volume representative of the plurality of data points; and
translating the virtual three-dimensional volume into implant forming commands.

6. The method of claim 5, wherein using the plurality of implant forming commands to form the implant comprises:
transmitting the implant forming commands to a controller;
using the controller to direct interactions between an implant forming system and an implant blank to replicate the virtual three-dimensional volume in the implant.

7. The method of claim 1, further comprising:
iteratively comparing the first shape of the void to a desired volumetric characteristic of the void to determine whether the operative end of the resection tool is at a desired boundary, wherein the desired volumetric characteristic is predefined and forms the desired boundary of the void; and
generating an anatomic shaping command if the operative end of the resection tool is at the desired boundary.

8. The method of claim 7, wherein the anatomic shaping command includes a command to cut power to the resection tool or a command to produce a visual indicator, an audio indicator, or a tactile indicator.

9. The method of claim 1, wherein monitoring removal of a portion of the anatomical structure includes collecting data on an amount of power flowing to the operative end of the resection tool.

10. The method of claim 1, wherein the operative end includes a unique identifier readable by the resection tool, and wherein the identifier is sent to a computer automatically when the operative end is attached to the resection tool and wherein the unique identifier includes a barcode, an RFID tag, or a magnet.

11. The method of claim 1, wherein the resection tool is controlled by a robotic arm during resection of tissue from the anatomical structure.

12. The method of claim 1, wherein determining a second shape includes acquiring a data set representing changes of the position and orientation of the operative end while the operative end resects tissue and wherein the data set is stored within a memory of a signal conversion system, and wherein a conversion software converts the data set into implant forming commands.

13. A method of repairing a tissue defect in an anatomical structure, the method comprising:
monitoring removal of a portion of the anatomical structure with a resection tool while the resection tool creates a void having a first shape, the portion including the tissue defect and the resection tool including a positional marker;
detecting an emanated signal from the positional marker to monitor movement of the resection tool and form a plurality of data points defining a second shape that substantially corresponds to the first shape of the void; and
after forming a plurality of data points, forming an implant having the second shape, wherein the implant is formed using implant forming commands translated from the plurality of data points.

14. The method of claim 13, wherein the emanated signal indicates a position and an orientation of an operative end of the resection tool.

15. The method of claim 13, further including creating a virtual three-dimensional volume representative of the plurality of data points.

16. The method of claim 13, wherein the implant is formed by an implant forming system that uses an implant blank to replicate the second shape.

17. The method of claim 13, further including monitoring milling of an articular surface of the implant after the implant has been implanted.

18. The method of claim 13, in combination with a method of resurfacing the implant, the method of resurfacing comprising:
collecting surface contour information of the anatomical structure before removing a portion of the anatomical structure, the surface contour information creating a virtual articular surface model;
translating the surface contour information into surface contour tolerance values;
after the implant has been implanted, monitoring a plurality of movements of the resection tool as the resection tool removes a portion of an articular surface of the implant while, wherein monitoring the plurality of movements of the resection tool includes creating a location signal representative of a location of the operative end of the resection tool;
iteratively comparing the location signal to the surface contour tolerance values to determine whether the operative end of the resection tool is in violation of the surface contour tolerance values; and
generating an implant resurfacing command if the operative end of the resection tool is in violation of the surface contour tolerance values.

19. The method of claim 13, wherein a second positional marker is located at a known spatial relationship to the anatomical structure.

20. The method of claim 19, further monitoring a second emanated signal from the second positional marker, wherein the second emanated signal indicates an orientation of the anatomical structure.

21. The method of claim 20, wherein the movement of the resecting tool creates a first movement vector and contemporaneous movement of the anatomical structure creates a second movement vector and wherein monitoring a plurality of movements of the resection tool includes subtracting the second movement vector from the first movement vector.

22. A method of repairing a tissue defect in an anatomical structure, the method comprising:
- monitoring removal of a portion of the anatomical structure with a resection tool while the resection tool creates a void having a first shape, the portion including the tissue defect and the resection tool having an operative end;
- monitoring a plurality of movements of the resection tool and creating a plurality of data points defining a second shape that corresponds to the first shape of the void, wherein monitoring the plurality of movements of the resection tool includes detecting an emanated signal from a positional marker coupled to the resection tool; and
- manufacturing an implant having the second shape for placement within the void, wherein manufacturing the implant includes translating the plurality of data points into a plurality of implant forming commands and using the implant forming commands to mill an implant blank into the implant.

* * * * *